United States Patent [19]

Clémence et al.

[11] 3,992,540

[45] Nov. 16, 1976

[54] 3-QUINOLINE-SUBSTITUTED 4-OXY-CARBOXAMIDES

[75] Inventors: Francois Clémence, Rosny-sous-Bois; Roger Deraedt, Pavillons-sous-Bois; André Allais, Gagny; Odile Le Martret, Paris, all of France

[73] Assignee: Roussel Uclaf, Paris, France

[22] Filed: July 28, 1975

[21] Appl. No.: 599,369

[30] Foreign Application Priority Data

Aug. 13, 1974 France .............................. 74.28038

[52] U.S. Cl. .............................. 424/258; 260/283 S; 260/287 AN
[51] Int. Cl.² ........................................ C07D 215/56
[58] Field of Search .............. 424/258; 260/287 AN, 260/287 F

[56] References Cited
UNITED STATES PATENTS

| | | | |
|---|---|---|---|
| 2,798,070 | 7/1957 | Cain | 260/287 F |
| 3,496,184 | 2/1970 | Mizzoni et al. | 260/287 AN |
| 3,524,858 | 8/1970 | Kaminsky et al. | 260/287 AN |

FOREIGN PATENTS OR APPLICATIONS

| | | | |
|---|---|---|---|
| 43-23948 | 10/1968 | Japan | 260/287 AN |

*Primary Examiner*—Nicholas S. Rizzo
*Assistant Examiner*—David E. Wheeler
*Attorney, Agent, or Firm*—Hammond & Littell

[57] ABSTRACT

Novel 3-quinoline-carboxamides of the formula

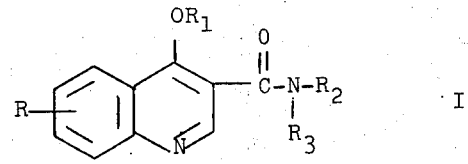

wherein R is selected from the group consisting of halogen, —CF₃, —OCF₃ and —SCF₃ in the 7- or 8-position, R₁ is selected from the group consisting of hydrogen and acyl of an aliphatic carboxylic acid of 2 to 4 carbon atoms, R₃ is selected from the group consisting of hydrogen and alkyl of 1 to 4 carbon atoms and R₂ is selected from the group consisting of thiazloyl, pyridinyl and oxazolyl and their non-toxic, pharmaceutically acceptable acid addition salts having analgesic activity and their preparation and novel intermediates.

16 Claims, No Drawings

3-QUINOLINE-SUBSTITUTED 4-OXY-CARBOXAMIDES

OBJECTS OF THE INVENTION

It is an object of the invention to provide novel 3-quinoline-carboxamides of formula I and their non-toxic, pharmaceutically acceptable acid addition salts.

It is another object of the invention to provide a novel process for the preparation of the products of formula I and to novel intermediates.

It is a further object of the invention to provide novel analgesic compositions and to a novel method of relieving pain in warm-blooded animals.

These and other objects and advantages of the invention will become obvious from the following detailed description.

THE INVENTION

The novel 3-quinoline-carboxamides of the invention are selected from the group consisting of compounds of the formula

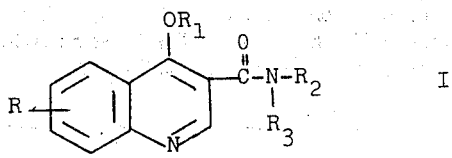

wherein R is selected from the group consisting of halogen, —$CF_3$, —$OCF_3$ and —$SCF_3$ in the 7- or 8-position, $R_1$ is selected from the group consisting of hydrogen and acyl of an aliphatic carboxylic acid of 2 to 4 carbon atoms, $R_3$ is selected from the group consisting of hydrogen and alkyl of 1 to 4 carbon atoms and $R_2$ is selected from the group consisting of thiazolyl, pyridinyl and oxazolyl and their non-toxic, pharmaceutically acceptable acid addition salts.

Among the preferred compounds of formula I are those where R is halogen such as chlorine, $R_1$ is acyl of an alkanoic acid of 2 to 4 carbon atoms such as acetyl and $R_3$ is alkyl of 1 to 4 carbon atoms such as methyl or ethyl. Other preferred compounds are those where R is chlorine or —$CF_3$, those where $R_1$ is hydrogen and those where $R_3$ is hydrogen as well as the non-toxic, pharmaceutically acceptable acid addition salts thereof.

Examples of suitable acids for the preparation of the acid addition salts are inorganic acids such as hydrochloric acid, hydrobromic acid, sulfuric acid, phosphoric acid, etc. and organic acids such as acetic acid, benzoic acid, tartaric acid, fumaric acid, maleic acid and sulfonic acids such as methanesulfonic acid or p-toluenesulfonic acid.

The novel process of the invention for the preparation of the compounds of formula I comprises reacting an acid derivative or free acid of the formula

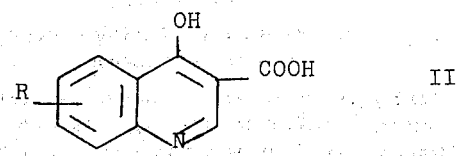

with a compound of the formula

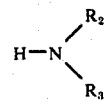

to obtain the corresponding compound of formula I wherein $R_1$ is hydrogen which may then be reacted with an acid to form the acid addition salt or reacted with an acylation agent of an acid of the formula $$HO-\overset{O}{\overset{\|}{C}}-R_1'$$

wherein $R'_1$ is alkyl of 1 to 3 carbon atoms to obtain the corresponding acylated compound of formula I which may be reacted with an acid to form the acid addition salt.

The derivative of the acid of formula II is preferably the acid chloride, lower alkyl esters, acid anhydride or mixed acid anhydride. The preferred agent is the acid chloride and the said reaction is effected in the presence of pyridine. The acids of formula II may be prepared by the process of Belgium Pat. No. 725,641.

The novel intermediate products of the invention are 4-hydroxy-8-trifluoromethyl-3-quinoline-carboxylic acid chloride, 4-hydroxy-8-chloro-3-quinoline-carboxylic acid chloride, 4-hydroxy-7-trifluoromethyl-3-quinoline-carboxylic acid chloride and 4-hydroxy-7-chloro-3-quinoline-carboxylic acid chloride.

The novel analgesic compositions of the invention are comprised of an effective amount of at least one compound of formula I and their non-toxic, pharmaceutically acceptable acid addition salts and a pharmaceutical carrier. The compositions may be in the form of injectable solutions or suspensions, tablets, capsules, gelules, drinkable solutions or emulsions or suppositories prepared in the usual manner.

The analgesic compositions are useful for the treatment of muscular, articular or nervous pain, of dental pains and migraines.

The novel method of the invention for relieving pain in warm-blooded animals comprises administering to warm-blooded animals an analgesically effective amount of at least one compound of formula I and their non-toxic, pharmaceutically acceptable acid addition salts. The products may be administered parenterally, rectally or orally. The usual useful dose is 1 to 40 mg/kg.

In the following examples there are described several preferred embodiments to illustrate the invention. However, it is to be understood that the invention is not intended to be limited to the specific embodiments.

EXAMPLE 1

N-[2-thiazolyl]-4-hydroxy-8-trifluoromethyl-3-quinoline-carboxamide

Step A: 4-hydroxy-8-trifluoromethyl-3-quinoline-carboxylic acid chloride

A mixture of 0.5 g of 4-hydroxy-8-trifluoromethyl-3-quinoline-carboxylic acid in 5 ml of thionyl chloride was stirred at room temperature for 24 hours and the precipitate formed was recovered by vacuum filtration to obtain 0.4 g of 4-hydroxy-8-trifluoromethyl-3-quinoline-carboxylic acid chloride melting at 222° C.

Step B: N-[2-thiazolyl]-4-hydroxy-8-trifluoromethyl-3-quinoline-carboxamide

| Analysis: | C₁₃H₈ClN₂S | | | | |
|---|---|---|---|---|---|
| Calculated: | %C 51.07 | %H 2.64 | %Cl 11.59 | %N 13.74 | %S 10.49 |
| Found: | 51.0 | 2.7 | 11.8 | 13.6 | 10.4 |

A mixture of 6.11 g of 2-amino-thiazole in 30 ml of pyridine was added with stirring to a mixture of 16.92 g of the acid chloride of Step A in 250 ml of pyridine and the resulting solution was stirred overnight. The pyridine was evaporated to obtain 27.77 g of a yellowish residue to which was added 100 ml of a 10% potassium carbonate solution and 25 ml of water. The resulting dispersion was stirred and vacuum filtered and the precipitate was washed with water and dried to obtain after crystallization 10.4 g of N-[2-thiazolyl]-4-hydroxy-8-trifluoromethyl-3-quinoline-carboxamide melting at 325° C.

EXAMPLE 2

N-[2-pyridinyl]-4-hydroxy-8-trifluoromethyl-3-quinoline-carboxamide

Using the procedure of Step B of Example 1, 4-hydroxy-8-trifluoromethyl-3-quinoline carboxylic acid chloride and 2-amino-pyridine were reacted to obtain N-[2-pyridinyl]-4-hydroxy-8-trifluoromethyl-3-quinoline-carboxamide melting at 335°–336° C.

EXAMPLE 3

N-[2-thiazolyl]-4-hydroxy-8-chloro-3-quinoline-carboxamide

Step A: 4-hydroxy-8-chloro-3-quinoline-carboxylic acid chloride

A mixture of 9.2 g of 4-hydroxy-8-chloro-3-quinoline-carboxylic acid in 100 ml of thionyl chloride was stirred at room temperature for 24 hours and was then vacuum filtered. The recovered precipitate was washed to obtain 0.4 g of 4-hydroxy-8-chloro-3-quinoline-carboxylic acid chloride melting at 258° C.

Step B: N-[2-thiazolyl]-4-hydroxy-8-chloro-3-quinoline-carboxamide

A solution of 2.9 g of 2-amino-thiazole in 20 ml of pyridine was added at room temperature to a suspension of 7 g of the acid chloride of Step A in 90 ml of pyridine and the mixture was stirred for 16 hours at room temperature. The pyridine was evaporated and a mixture of potassium carbonate solution and water was added to the residue. The reaction mixture was stirred and vacuum filtered and the recovered precipitate was washed and dried. The product was crystallized from dimethylformamide to obtain 6.5 g of N-[2-thiazolyl]-4-hydroxy-8-chloro-3-quinoline-carboxamide melting above 369° C.

EXAMPLE 4

N-[2-thiazolyl]-4-hydroxy-7-trifluoromethyl-3-quinoline-carboxamide

Step A: 4-hydroxy-7-trifluoromethyl-3-quinoline-carboxylic acid chloride

Using the procedure of Step A of Example 1, 4-hydroxy-7-trifluoromethyl-3-quinoline-carboxylic acid was reacted to obtain 4-hydroxy-7-trifluoromethyl-3-quinoline-carboxylic acid chloride melting at 323° C.

Step B: N-[2-thiazolyl]-4-hydroxy-7-trifluoromethyl-3-quinoline-carboxamide

Using the procedure of Step B of Example 1, 3.7 g of the acid chloride of Step A and 1.35 g of 2-amino-thiazole were reacted to obtain 2.58 g of N-[2-thiazolyl]-4-hydroxy-7-trifluoromethyl-3-quinoline-carboxamide melting above 369° C.

| Analysis: | C₁₄H₈N₂F₃S | | | | |
|---|---|---|---|---|---|
| Calculated: | %C 49.56 | %H 2.38 | %F 16.80 | %N 12.38 | %S 9.45 |
| Found: | 49.9 | 2.4 | 16.7 | 12.6 | 9.5 |

EXAMPLE 5

N-[2-thiazolyl]-4-hydroxy-7-chloro-3-quinoline-carboxamide

Step A: 4-hydroxy-7-chloro-3-quinoline-carboxylic acid chloride

Using the procedure of Example 1, Step A, 4-hydroxy-7-chloro-3-quinoline-carboxylic acid was reacted to form the corresponding acid chloride melting at 370° C.

Step B: N-[2-thiazolyl]-4-hydroxy-7-chloro-3-quinoline-carboxamide

The acid chloride of Step A and 2-amino thiazole were reacted as in Step B of Example 1 to obtain N-[2-thiazolyl]-4-hydroxy-7-chloro-3-quinoline-carboxamide greater than 370° C.

| Analysis: | C₁₃H₈ClN₃S | | | | |
|---|---|---|---|---|---|
| Calculated: | %C 51.07 | %H 2.64 | %Cl 11.59 | %N 13.74 | %S 10.49 |
| Found: | 51.1 | 2.6 | 11.6 | 13.6 | 10.7 |

EXAMPLE 6

N-[2-oxazolyl]-4-hydroxy-8-trifluoromethyl-3-quinoline-carboxamide

Using the procedure of Step B of Example 1, 4-hydroxy-8-trifluoromethyl-3-quinoline-carboxylic acid chloride and 2-amino-oxazole were reacted to obtain N-[2-oxazolyl]-4-hydroxy-8-trifluoromethyl-3-quinoline-carboxamide melting at 304° C.

EXAMPLE 7

N-methyl-N-[2-thiazolyl]-4-hydroxy-8-trifluoromethyl-3-quinoline-carboxamide

Using the procedure of Step B of Example 1, 4-hydroxy-8-trifluoromethyl-3-quinoline-carboxylic acid chloride and N-methyl-2-amino-thiazole were reacted to form N-methyl-N-[2-thiazolyl]-4-hydroxy-8-trifluoromethyl-3-quinoline-carboxamide.

EXAMPLE 8

Tablets were prepared in the usual manner with 50 mg of N-[2-thiazolyl]-4-hydroxy-8-trifluoromethyl-3-quinoline-carboxamide and 350 mg of an excipient of lactose, talc, starch and magnesium stearate.

PHARMACOLOGICAL DATA

A. Analgesic Activity

The test was based on that of Koster et al [Fed. Proc., Vol. 18 (1959), p. 412] in which the intraperitoneal injection of acetic acid to mice provokes repeated stretching and twisting movements which persist for more than 6 hours. Analgesics prevent or suspress these syndromes which are considered to be an exteriorization of a diffuse abdominal pain. A 1% solution of acetic acid in water was used at a dose of 0.01 ml/g or 100 mg/kg of acetic acid to release the syndrome.

The test product was orally administered 30 minutes before the acetic acid injection and the mice were fasted for 24 hours before the start of the test. The stretchings for the mice were observed and totaled for each mouse in a 15 minutes observation period starting just after the acetic acid injection. The results were expressed as $DA_{50}$, that dose which reduced by 50% the number of stretchings as compared to the controls and the $DA_{50}$ for N-[2-thiazolyl]-4-hydroxy-8-trifluoromethyl-3-quinoline-carboxamide was 5 mg/kg; for N-[2-thiazolyl]-4-hydroxy-8-chloro-3-quinoline-carboxamide was 4 mg/kg; and for N-[2-thiazolyl]-4-hydroxy-7-trifluoromethyl-3-quinoline-carboxamide was 7 mg/kg.

B. Acute toxicity

The acute toxicity was determined on groups of 10 mice weighing between 18–22 g and the test product was administered intraperitoneally in increasing dose in suspensions at 0.25% in carboxymethyl-cellulose added of Tween 80. The animals were observed for a week and the $DL_{50}$ was graphically determined by the Miller et al method for N-/2-thiazolyl/-4-hydroxy-8-trifluoromethyl-3-quinoline-carboxamide to be 225 mg/Kg. When orally administered, the said product was very well tolerated at a dose of 500 mg/Kg.

Various modifications of the compositions and methods of the invention may be made without departing from the spirit or scope thereof and it should be understood that the invention is intended to be limited only as defined in the appended claims.

We claim:

1. A compound selected from the group consisting of compounds of the formula

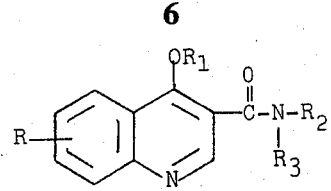

wherein R is selected from the group consisting of halogen, —$CF_3$, —$OCF_3$ and —$SCF_3$ in the 7- or 8-position, $R_1$ is selected from the group consisting of hydrogen and acyl of an aliphatic carboxylic acid of 2 to 4 carbon atoms, $R_3$ is selected from the group consisting of hydrogen and alkyl of 1 to 4 carbon atoms and $R_2$ is selected from the group consisting of thiazolyl, pyridinyl and oxazolyl and their non-toxic, pharmaceutically acceptable acid addition salts.

2. A compound of claim 1 wherein R is chlorine or trifluoromethyl.

3. A compound of claim 1 wherein $R_1$ is hydrogen.

4. A compound of claim 1 wherein $R_3$ is hydrogen.

5. A compound of claim 1 selected from the group consisting of N-[2-thiazolyl]-4-hydroxy-8-trifluoromethyl-3-quinoline-carboxamide and its non-toxic, pharmaceutically acceptable acid addition salts.

6. A compound of claim 1 selected from the group consisting of N-[2-pyridinyl]-4-hydroxy-8-trifluoromethyl-3-quinoline-carboxamide and its non-toxic, pharmaceutically acceptable acid addition salts.

7. A compound of claim 1 selected from the group consisting of N-[2-thiazolyl]-4-hydroxy-8-chloro-3-quinoline-carboxamide and its non-toxic, pharmaceutically acceptable acid addition salts.

8. A compound of claim 1 selected from the group consisting of N-[2-thiazolyl]-4-hydroxy-7-trifluoromethyl-3-quinoline-carboxamide and its non-toxic, pharmaceutically acceptable acid addition salts.

9. A compound of claim 1 selected from the group consisting of N-[2-thiazolyl]-4-hydroxy-7-chloro-3-quinoline-carboxamide and its non-toxic, pharmaceutically acceptable acid addition salts.

10. A compound of claim 1 selected from the group consisting of N-[2-oxazolyl]-4-hydroxy-8-trifluoromethyl-3-quinoline-carboxamide and its non-toxic, pharmaceutically acceptable acid addition salts.

11. A compound selected from the group consisting of 4-hydroxy-8-trifluoromethyl-3-quinoline-carboxylic acid chloride, 4-hydroxy-8-chloro-3-quinoline-carboxylic acid chloride, 4-hydroxy-7-trifluoromethyl-3-quinoline-carboxylic acid chloride and 4-hydroxy-7-chloro-3-quinoline-carboxylic acid chloride.

12. An analgesic composition comprising an analgesically effective amount of a compound of claim 1 and an inert pharmaceutical carrier.

13. A method of relieving pain in warm-blooded animals comprising administering to warm-blooded animals an analgesically effective amount of a compound of claim 1.

14. The method of claim 13 wherein R is chlorine or —$CF_3$.

15. The method of claim 13 wherein $R_1$ is hydrogen.

16. The method of claim 13 wherein $R_3$ is hydrogen.

* * * * *